United States Patent [19]

McAndrew

[11] 4,373,913
[45] Feb. 15, 1983

[54] CFC EXPANSION ARCH

[76] Inventor: James R. McAndrew, 3233 Sherwood Forest Blvd., Suite 202, Baton Rouge, La. 70816

[21] Appl. No.: 264,036

[22] Filed: May 15, 1981

[51] Int. Cl.³ .............................................. A61C 3/00
[52] U.S. Cl. ........................................ 433/7; 433/21; 433/23
[58] Field of Search ................ 433/7, 18, 21, 23, 24, 433/19

[56] References Cited

U.S. PATENT DOCUMENTS

| 1,504,942 | 8/1924 | Comegys | 433/7 |
| 1,773,588 | 8/1930 | Linde | 433/7 |
| 2,062,395 | 12/1936 | Brusse et al. | 433/23 |
| 2,262,108 | 11/1941 | Linde | 433/7 |
| 3,162,948 | 12/1964 | Gerber | 433/7 |
| 3,618,214 | 11/1971 | Armstrong | 433/19 |

OTHER PUBLICATIONS

"Barnet Jaffe" ad, American Jour. of Orthodontia, vol. 55, Jan.-Mar., 1969, p. 4.
"Williams" Gold Refining Co. ad, American Jour. of Orthodontia, vol. 43, Jan.-Jun., 1957.

Primary Examiner—Gene Mancene
Assistant Examiner—John J. Wilson
Attorney, Agent, or Firm—Roy, Kiesel, Patterson & McKay

[57] ABSTRACT

A continuous force control arch expander for use in orthodontics is provided comprising a set of anchor bands with expansion wires rigidly and tangentially attached to said anchor bands.

3 Claims, 3 Drawing Figures

CFC EXPANSION ARCH

BACKGROUND OF THE INVENTION

1. Field of the Invention

This invention relates generally to orthodontic appliances and more particularly to devices for expanding the maxillary arch.

2. Prior Art

A number of orthodontic appliances have been developed over the years to shape and contour the teeth. These include devices to shape the maxillary arch for proper bite. A typical example of such devices in U.S. Pat. No. 3,618,214, invented by Armstrong, issued Nov. 9, 1971, entitled "Coiled Wire Spring Appliances for use in Orthodontics".

The purpose of these devices is to provide light continuous force in the appropriate direction to control growth of teeth. There are a number of problems associated with these appliances as they exist at the present time.

First, these devices often require multiple adjustments for effectiveness. They do not provide continuous even force but rather have a force which tends to diminish with use. Additionally, because of the numerous pieces used, they make proper hygiene extremely difficult. The numerous anchor pieces also have a tendency to cut into the teeth and gums with pain resulting. Finally, these devices are very visible in the mouth and are uncosmetic.

SUMMARY OF THE INVENTION

Therefore one object of this invention is to provide a device for expanding the maxillary arch which produces continuous controlled force applied to the teeth.

It is an additional object of this invention to provide such a device which only requires activation of the applied force on installation.

Still another object of this invention is to provide a maxillary arch expander which is relatively simple in application thus reducing the inhibitory effect on dental hygiene.

Still an additional object of this invention is to provide a device which accomplishes the expansion effect with a minimum of pain.

Another object of this invention is to provide a maxillary arch expander which is unobtrusive and cosmetic.

Other objects and advantages of this invention shall become apparent from the ensuing descriptions of the invention.

Accordingly, a continuous force control arch expander for use in orthodontics is provided comprising a set of anchor bands for attachment to the rear molars, and a corresponding set of expansion wires rigidly and tangentially attached to said anchor bands and applied to the interior of the teeth.

PREFERRED EMBODIMENTS

Figure 1:
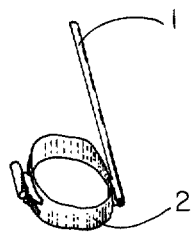
FIG. 1 is a side perspective view of a single anchor band and attached expansion wire.

Without limiting the scope of this invention, the preferred features of this invention will be described using particular preferred embodiments of the invention. Referring to FIG. 1, expansion wire 1 is rigidly attached by methods currently employed in the art (i.e. soldering) to anchor band 2 at a tangent. In this particular embodiment, expansion wire 1 is of 030 gauge.

Figure 2:
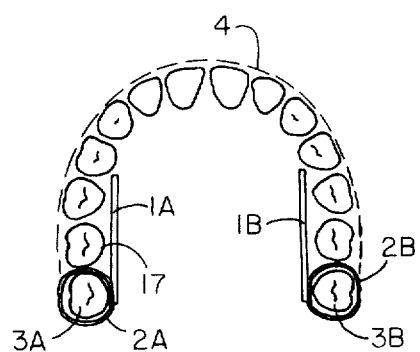
FIG. 2 is an overhead view of the invention as applied.

Referring now to FIG. 2, anchor bands 2A and 2B are fitted around molars 3A and 3B, respectively, so that expansion wires 1A and 1B extend forward along the interior of the tooth line generally denoted as 4 and exert a continuous force against the interior teeth wall surface 17. Anchor bands 2A and 2B are then rotated outwardly until expansion wires 1A and 1B are exerting the desired force on tooth line 4. Then anchor bands 2A and 2B are tightened by methods currently employed in the art.

Figure 3:
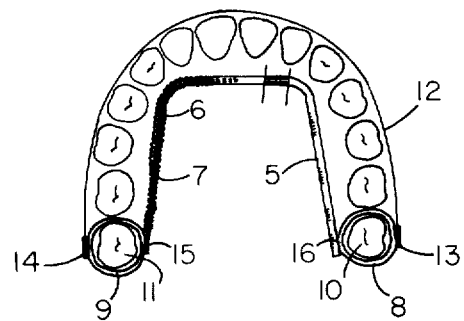
FIG. 3 is an overhead view of a preferred embodiment of the invention as applied.

Referring now to FIG. 3, in a preferred feature, expansion wire 1A is replaced by expansion tube 5, a small gauge metal tube which is angled at 90 degrees as shown. Expansion wire 6 is of a gauge small enough to fit into expansion tube 5 and is also angled at 90 degrees as shown in FIG. 3. Additionally spring 7 is fitted around expansion wire 6. Spring 7 must have an interior diameter large enough to encircle expansion wire 6 but not large enough to encircle expansion tube 5. Anchor bands 8 and 9 are then fitted around molars 10 and 11 respectively, with expansion wire 6 being fitted into expansion tube 5 and spring 7 being compressed. This compression provides additional expansion force and increases the efficiency of the invention.

Still referring to FIG. 3 and in another preferred feature, control wire 12 is rigidly attached to anchor bands 8 and 9 at points 13 and 14 which are opposite expansion wire 6 and expansion tube 5 points of attachment 15 and 16. Then control wire 12 is tightened by methods currently employed in the art to provide additional control means of the arch expansion. There are, of course, many obvious alternate embodiments and modifications to this invention which are intended to be included within the scope of this invention as described by the following claims:

What I claim is:

1. A continuous force control arch expander for use in orthodontics comprising:
   A. A set of anchor bands for fixed attachment to molar teeth on opposite sides of the arch,
   B. a pair of expansion wires rigidly and tangentially attached one each to said anchor bands having means for placement of a continuous expansion force against the interior surface wall of teeth, and
   C. a control wire fixedly attached at its opposite ends to said anchor bands in a position to be fitted about the outside of the tooth line.

2. A continuous force control arch expander for use in orthodonics comprising:
   A. a set of anchor bands for attachment to molar teeth;
   B. an expansion wire rigidly and tangentially attached at one end to one of said anchor bands and having its opposite end bent in arcuate fashion to mate in a cavity located in one end of an expansion tube, said expansion tube rigedly and tangentially attached at its opposite end to the other anchor band and being bent in arcuate fashion for alignment of its cavity with said expansion wire end; and,
   C. a coil spring fitting about said expansion wire, said spring having one of its ends abutting against the expansion wire anchor band and having its opposite end abutting against the expansion tube cavity end forcing the wires to push outward against the teeth with a continuous force.

3. A continuous force control arch expander according to claim 2 wherein a control wire is fixedly attached at its opposite ends to said anchor bands in a position to be fitted about the outside of the tooth line.

* * * * *